United States Patent
Tafu et al.

(10) Patent No.: US 6,884,456 B2
(45) Date of Patent: Apr. 26, 2005

(54) HIGH-MINERAL OYSTER EXTRACT AND A PROCESS FOR MANUFACTURING THE SAME

(75) Inventors: Satoshi Tafu, Kyoto (JP); Yoshikazu Matsuda, Kyoto (JP)

(73) Assignee: Japan Clinic Co., Ltd., Kyoto (JP)

( * ) Notice: Subject to any disclaimer, the term of this patent is extended or adjusted under 35 U.S.C. 154(b) by 0 days.

(21) Appl. No.: 10/767,698

(22) Filed: Jan. 29, 2004

(65) Prior Publication Data

US 2004/0185166 A1 Sep. 23, 2004

Related U.S. Application Data

(62) Division of application No. 09/834,290, filed on Apr. 12, 2001.

(30) Foreign Application Priority Data

Apr. 12, 2000 (JP) ........................................ 2000-110882

(51) Int. Cl.[7] ........................... A23L 1/327; A23L 1/333
(52) U.S. Cl. ........................ 426/643; 426/437; 426/478; 426/655
(58) Field of Search ................................. 426/437, 478, 426/643, 655

(56) References Cited

U.S. PATENT DOCUMENTS

| | | | | |
|---|---|---|---|---|
| 4,770,894 A | * | 9/1988 | Usui et al. | 426/655 |
| 5,271,951 A | * | 12/1993 | Ando | 426/655 |
| 5,958,477 A | * | 9/1999 | Muromachi et al. | 426/74 |

* cited by examiner

*Primary Examiner*—Arthur L. Corbin
(74) *Attorney, Agent, or Firm*—Flynn, Thiel, Boutell & Tanis, P.C.

(57) ABSTRACT

The present invention provides a process for extracting minerals from mineral-rich oysters and furthermore provides an oyster extract containing the minerals, and taurine, glycogen, and nucleotides.

First, raw oysters are subjected to hot water extraction to obtain soluble ingredients and to remove unwanted components, and then the residue is extracted with acid solution of pH 2 to 4. The extract is neutralized with alkali to obtain a precipitate having a high content of minerals such as zinc. The oyster extract obtained by this process contains zinc in the amount of 6% to 13% by dry weight.

1 Claim, 2 Drawing Sheets

HIGH-MINERAL OYSTER EXTRACT AND A PROCESS FOR MANUFACTURING THE SAME

This application is a DIV of Ser. No. 09/834,290 filed Apr. 12, 2001.

FIELD OF THE INVENTION

The present invention relates to an oyster extract containing large amounts of minerals such as zinc and manganese, and also relates to a process for manufacturing the same.

BACKGROUND OF THE INVENTION

Recently, minerals have become recognized as important elements for human health. For example, a deficiency of zinc or manganese causes taste abnormality or growth disorder of the human body. This deficiency is caused by a change in the kinds of food eaten or in eating habits. It is very important to take these minerals every day for preventing diseases.

The oyster, or *Crassostrea gigas* is well known as a perfect nutritious food, because it contains large amounts of nutritious components compared with other foods. However, it is not advisable to take oysters as daily food, because they tend to cause allergy and because of the accumulation of heavy metals contained in oysters. In addition, the ingredients of the oysters change depending on the season or place from which they were harvested.

To solve these problems, oyster extract tablets have been developed and marketed as a healthy food, which tablets are generally prepared by extracting oysters with water or hot water as disclosed in Japanese Patent Publication Kokoku Hei 4-63672(1992-63672 B2). In this method, an oyster extract is obtained by hot water extraction at 50 to 90° C. for 2 to 3 hours, and ethanol is then added to the extract to obtain a precipitate.

Although water soluble ingredients such as taurine, glycogen, and other substances are extracted with water, water-insoluble minerals such as zinc, manganese, and other minerals can not be extracted by water or hot water. Therefore, large amounts of minerals remain in the residue of the oyster extracted by these means.

DESCRIPTION OF THE INVENTION

One objective of the present invention is to provide an oyster extract rich in minerals, which thus requires an effective extraction process for water-insoluble minerals such as zinc and manganese from the oyster extract residue.

Another objective of this invention is to provide an oyster extract containing the conventional components of the oyster extract, such as taurine, glycogen, and nucleotides, and the minerals mentioned above.

The present invention is based on the finding that water-insoluble ingredients contained in oyster, such as zinc, manganese, and other minerals, can be extracted under acidic conditions, more particularly by adding acid to the oyster residue after hot water extraction.

A nutritious oyster extract is obtained by mixing the oyster water-soluble extract containing taurine, glycogen, and nucleotides as main ingredients disclosed in prior arts with water-insoluble extract containing minerals such as zinc, manganese, and other minerals prepared by the method mentioned above.

EMBODIMENTS OF THE INVENTION

Figure 1:
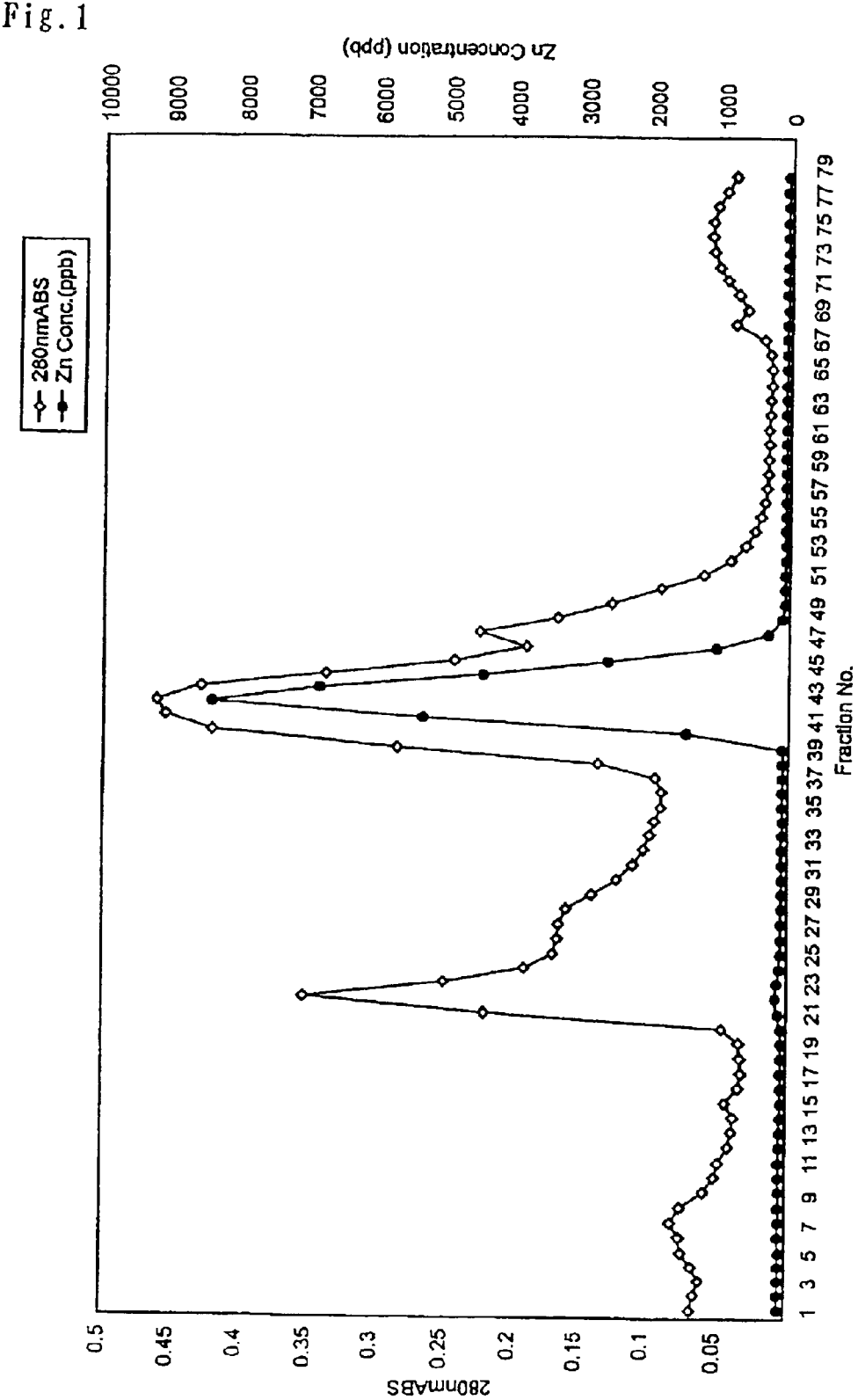
FIG. 1 shows a gel filtration chromatography pattern and zinc concentration in each fraction, obtained from a high-mineral oyster extract of the present invention.

Oysters are first extracted with hot water, and then the oyster residue is extracted with an acid solution of pH from 2 to 4. Thereafter, the pH of the extract is brought to neutral to obtain a precipitate of the oyster extract.

As disclosed in Japanese Patent Publication Kokoku Hei 4-63672(1992-63672 B2), an oyster extract is obtained by hot water extraction at 50 to 90° C. for 2 to 3 hours, and ethanol is added to the extract to obtain a precipitate. The precipitate is condensed to 20% to 45% by dry weight. The extract contains taurine, glycogen and nucleotides.

Then the oyster residue from the hot water extraction is subjected to acid extraction.

If the oysters are extracted directly with acid solution, the proteins of the oyster are hydrolyzed at the high temperature, and the heavy metals contained in the internal organs of the oysters, chlorophyll-related substances, and unwanted proteins become a part of the extract.

Further, the useful ingredients are diluted and noxious ingredients are extracted by the direct acid extraction. In addition, the main ingredients disclosed in prior arts such as glycogen and nucleotide materials are denatured by the acid. Therefore, it is essential to employ the hot water extraction, which is effective to obtain water-soluble substances from oysters, prior to the acid extraction.

Any acid is applicable to the present invention, for instance, hydrochloric acid, sulfuric acid or phosphoric acid as inorganic acids, and citric acid or acetic acid, as organic acids.

It is not necessary to specify the concentration and the volume of the acid solution.

The pH of the oyster residue is adjusted to 1 to 4, or 2 to 3 preferably, after adding the acid solution to the oyster residue, and if the pH exceeds 4, the extraction efficiency of minerals is reduced, because the raw oysters spontaneously buffer the change of pH, bringing the pH of the solution to neutral.

The minimum extraction time is at least 1 hour, preferably 24 hours.

The temperature for the extraction is not specified, but room temperature is preferable. If the temperature is low, the extraction efficiency is decreased. On the contrary, if the temperature is high, the oysters are degraded and unwanted substances are extracted.

After the acid extraction, a solid-liquid separation procedure is conducted, for instance, filtration or centrifugation. The solid component, which is separated from the extract, is about 2% to 5% of the extract.

The extract is neutralized by adding alkali, and a precipitate is obtained. The precipate is then centrifuged, and washed with water to remove the unwanted salts. The solid component, having a high content of minerals is obtained after drying.

Preferable alkalis for neutralization are NaOH and KOH.

The oyster extract contains a large amount of zinc, 6% to 14% by dry weight. The preferable zinc range is 10% to 14%, or 12% to 14% by dry weight.

According to the analysis by gel filtration chromatography of the acid extract from raw oysters, zinc is found in high concentration in the fractions of 3000 to 5000 daltons as molecular weight and in those over 8000. Therefore, zinc might be combined with various organic substances of raw oysters.

FIG. 1 shows the relation between the gel filtration chromatography pattern of the high-mineral oyster extract of the present invention and the zinc concentration in each fraction.

As shown in FIG. 1, the largest amount of zinc is eluted in the fraction of 3000 to 5000 daltons as molecular weight (fractions nos. 39 to 49 in FIG. 1).

Figure 2:
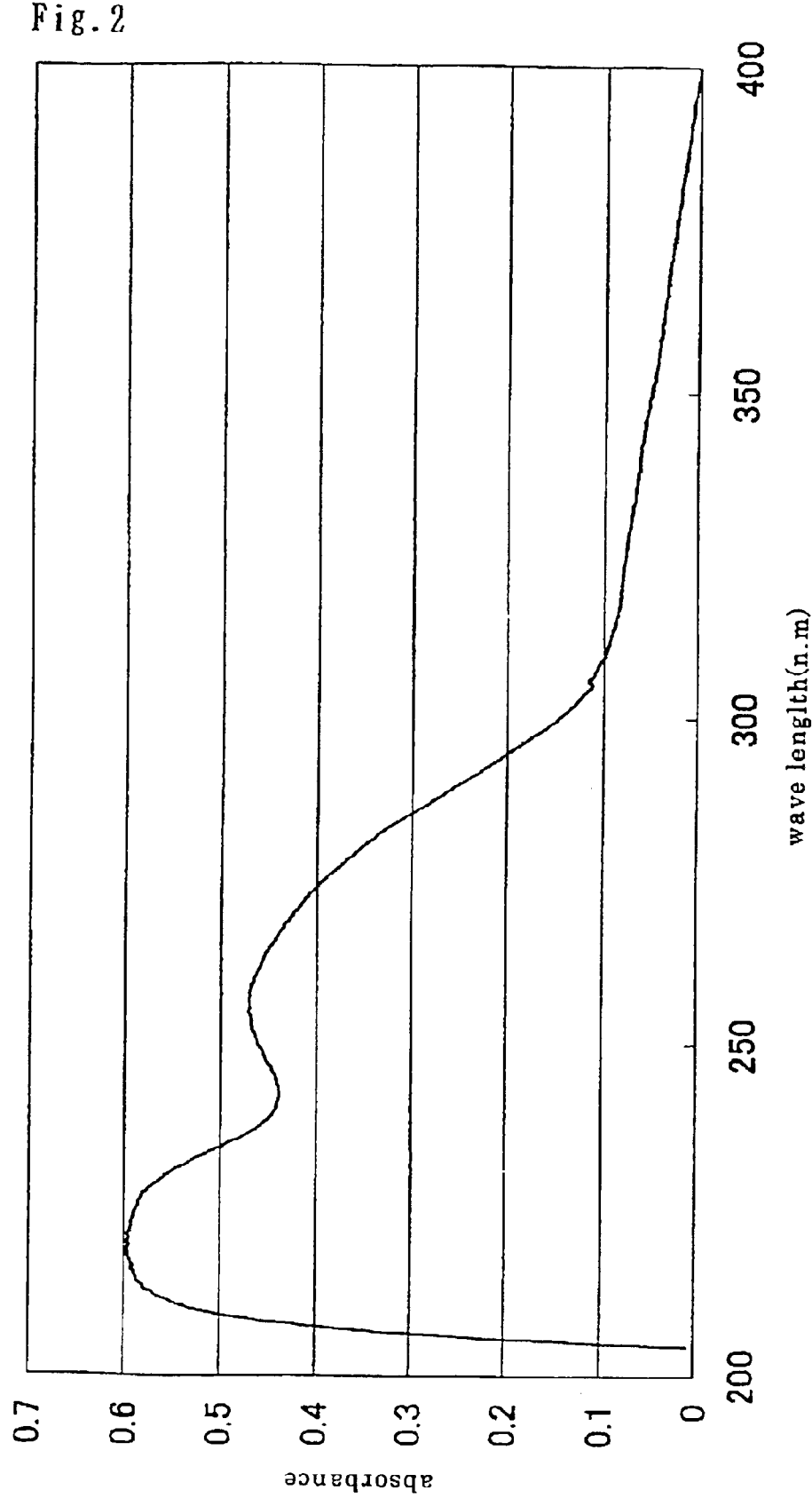
FIG. 2 shows the UV absorption spectrum of a fraction ranging from 3000 to 5000 daltons in molecular weight, which was separated from the high-mineral oyster extract of the present invention.

FIG. 2 shows the UV absorption spectrum of the fraction of 3000 to 5000 daltons as molecular weight, separated from the high-mineral oyster extract of the present invention.

As shown in FIG. 2, the absorption peaks in the UV spectrum are observed at 257 nm and 219 nm.

In the high-mineral oyster extract of this invention, zinc is possibly combined with a peptide of 3000 to 5000 daltons in the ratio of 1:1.

Besides the zinc, magnesium, calcium and manganese are also contained in the high-mineral oyster extract of the present invention. Among these minerals, calcium and manganese, like zinc, might also be combined with the water-insoluble protein.

The extract obtained by this method contains highly concentrated minerals, zinc is 4 to 6 times as much, and manganese, calcium, and magnesium are 2 to 3 times as much, by dry weight as contained in the raw oyster. The oyster extract according to this invention contains manganese in the amount of 0.05% to 0.2% by dry weight.

The high-mineral oyster extract of the present invention may be mixed with the conventional oyster extract, such as the extract obtained by the hot water extraction.

The mixture of these two extracts is a highly balanced nutritious oyster extract containing minerals such as zinc and other nutritious components, such as taurine, glycogen, and nucleotides.

The mixture ratio of the high-mineral oyster extract and the conventional oyster extract is selectively determined depending on the desired mineral level. For example, it is preferable to mix the two at a ratio of 1 to 40(high-mineral/conventional).

The preferable zinc level in the oyster extract mixture is 0.05% to 0.4%, more preferably 0.2% to 0.4% or much more preferably 0.3% to 0.4% by dry weight. The preferable taurine level is 3% to 7%, more preferably 4% to 7% preferably, or much more preferably 5% to 7% by dry weight.

The mixture contains glycogen in amount of 30% to 60%, or 40% to 60% preferably, or 50% to 60% by dry weight more preferably. The preferable manganese level is 0.002% to 0.005%, more preferably 0.003% to 0.005% or much more preferably 0.004% to 0.005% by dry weight. The preferable magnesium level is 0.4% to 1.2%, more preferably 0.5% to 1.2%, or much more preferably 0.6% to 1.2% by dry weight.

The invention is explained in more detail with the following embodiments of this invention, however, the present invention is not restricted to the embodiments.

EXAMPLE 1

The raw oyster of 37.5 g by dry weight is extracted with 65 g of hot water of 80° C. for 3 hours. Thereby 8.4 g of oyster extract by dry weight is obtained.

For obtaining a high-mineral oyster extract, 0.1N.HCl is added to the oyster residue which is kept at a room temperature. After 24 hours, the extract is filtered and neutralized by adding NaOH to obtain a precipitate. The precipitate is centrifuged for removing water from the extract and washed with water to remove the unwanted salts. The precipitate is then heated to obtain the dried oyster extract.

Finally, 0.2 g by dry weight of oyster extract, which contains a high content of minerals, is obtained.

The compositions of each extract are shown in Table 1.

TABLE 1

| | Ash (%) | Yield (g) | Zn (ppm) | Mn (ppm) | Mg (ppm) | Ca (ppm) | Taurine (Wt. %) | Glycogen (Wt. %) |
|---|---|---|---|---|---|---|---|---|
| Raw oyster | 20.3 | 37.5 | 2,568 | 84 | 5,717 | 1,453 | 3.50 | 33.0 |
| Residue (hot water extraction) | 7.6 | 20.7 | 3,565 | 58 | 2,639 | 697 | 3.47 | 0.6 |
| Extract (A) | 35.6 | 8.4 | 582 | 32 | 8,171 | 590 | 4.05 | 43.5 |
| High-mineral Extract (B) | 41.9 | 0.2 | 133,223 | 1,012 | 11,619 | 4,102 | 0.04 | 0.4 |
| Mixture (A) + (B) (42:1) | | | 3,692 | 55 | 8,249 | | 3.96 | 42.5 |

As indicated in Table 1, the extract contains 5 times as much zinc as raw oysters, 12 times as much manganese, 2 to 3 times as much magnesium and calcium.

The nutritious oyster extract mixture is obtained by mixing the hot water extract and the acid extract at a mixture ratio of 42 to 1, as shown in Table 1.

By our invention, it now becomes possible to obtain an oyster extract containing large amounts of minerals such as zinc and manganese. Furthermore an oyster extract that contains both the minerals such as zinc or manganese and water-soluble components such as taurine, glycogen, and nucleotides is obtained.

What is claimed:

1. A process for manufacturing an oyster extract comprising the steps of subjecting oysters to hot water extraction to produce an oyster residue; subjecting the oyster residue to acid extraction with an acid solution having a pH of from 2 to 4 to produce a residue extract having a pH of 2 to 4; filtering the residue extract to form a filtered extract and then neutralizing the pH of the filtered extract to obtain a high mineral oyster extract.

* * * * *